United States Patent [19]

Wieland et al.

[11] Patent Number: 5,077,035

[45] Date of Patent: Dec. 31, 1991

[54] RADIOIODINATED BENZOVESAMICOL ANALOGS FOR CHOLINERGIC NERVE MAPPING

[75] Inventors: Donald M. Wieland; Yong-Woon Jung; Marcian E. Van Dort; David L. Gildersleeve, all of Ann Arbor, Mich.

[73] Assignee: The University of Michigan, Ann Arbor, Mich.

[21] Appl. No.: 523,233

[22] Filed: May 14, 1990

[51] Int. Cl.$^5$ .................... A61K 49/02; C07D 211/06
[52] U.S. Cl. ................................. 424/1.1; 546/206
[58] Field of Search ..................... 424/1.1; 546/206

[56] References Cited

U.S. PATENT DOCUMENTS 4,246,268 1/1981 Carr ........................... 546/206 X
4,435,570 3/1984 Nishimura et al. ............ 424/1.1 X

OTHER PUBLICATIONS

Rogers et al., *J. Med. Chem.*, vol. 32, No. 6, pp. 1217-1230, (1989).

*Primary Examiner*—John S. Maples
*Attorney, Agent, or Firm*—Rohm & Monsanto

[57] ABSTRACT

Radioiodinated benzovesamicol analogs which selectively localize in presynaptic cholinergic neurons of the general formula:

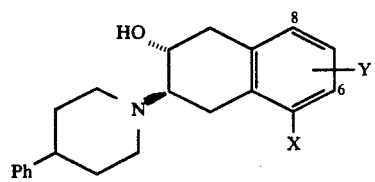

where X is selected from the group consisting of H, OH, NH$_2$, NHCO-3-[I]-Ph, and a radioactive isotope of iodine, and Y is selected from the group of H and a radioactive isotope of iodine, Y being H is X contains iodine. Illustrative examples include: (±)-trans-2-hydroxy-5-iodo-3-(4-phenylpiperidino)tetralin; (±)-trans-3-hydroxy-5-iodo-2-(4-phenylpiperidino)tetralin; (±)-trans-5-amino-2-hydroxy-8-iodo-3-(4-phenylpiperidino)tetralin; and (±)-trans-2-hydroxy-5-(3-iodobenzamido)-3-(4-phenylpiperidino)tetralin. The novel radioiodinated benzovesamicol analogs may be used as radiopharmaceuticals to visualize cholinergic neurons with conventional imaging devices which are typically found in most nuclear medicine or radiology clinics.

15 Claims, 4 Drawing Sheets

RADIOIODINATED BENZOVESAMICOL ANALOGS FOR CHOLINERGIC NERVE MAPPING

GOVERNMENT RIGHTS

This invention was made with Government support under Research Grant No. 5 RO1 NS25656-02 awarded by the National Institutes of Health. The Government has certain rights in this invention.

BACKGROUND OF THE INVENTION

This invention relates generally to radioactive compounds which are useful as radiopharmaceuticals, and more particularly, to radioiodinated benzovesamicol analogs which selectively localize in presynaptic cholinergic neurons.

Alzheimer's disease, which is often characterized by the degeneration of the cholinergic nerves, is increasingly prevalent as the mean age of the American population increases. It has been estimated that there are approximately between 5 and 6 million persons in the United States afflicted with Alzheimer's disease.

It would be highly desirable to be able to image cholinergic nerves to assess the extent and regional pattern of nerve damage in Alzheimer patients. Moreover, such brain imaging would be useful for diagnosing and monitoring patients with rarer neurological disorders, such as olivopontocerebellar atrophy, progressive supranuclear palsy, and patients demented by Parkinson's disease.

In the present state of the art, patients with Alzheimer's disease and related neurological disorders, are being imaged with radiopharmaceuticals which are indicators of brain blood flow or brain metabolism. Positron emission tomography (PET) studies have revealed that patients with clinically diagnosed Alzheimer's disease have reduced metabolism and perfusion, particularly in the posterior parietal and in the frontal regions of the brain. Moreover, PET studies have demonstrated that a significant increase in right/left metabolic asymmetry is associated with predominantly lateralized neuropsychological deficits.

Single photon emission computed tomography (SPECT) perfusion studies of regional blood flow have been done with a xenon-133 inhalation method and with intravenous administration of N-isopropyl-$^{123}$I iodoamphetamine. More recently, technetium-99m hexamethylpropylenamine oxime has been utilized as a tracer for SPECT studies inasmuch as it crosses the blood-brain barrier and is completely cleared from the blood in a single passage through the cerebral circulation so that regional distribution is proportionate to regional blood flow.

The known radiotracers for brain imaging are lipophilic, and therefore move across the blood-brain barrier with nearly complete extraction during a single pass through the cerebral circulation. Once inside, however, these radiotracers bind to nonspecific receptors, or are metabolized to non-lipophilic compounds. It is an unfortunate characteristic of these radiopharmaceuticals that they do not localize in the brain based on their affinity for presynaptic cholinergic neurons.

The most consistent and profound of the currently recognized changes in patients afflicted with Alzheimer's disease involves the acetylcholine-containing neurons projecting from the basal forebrain nuclei to cerebral cortex and other forebrain areas. Reductions in the activity of choline acetyltransferase, an enzyme marker for cholinergic neurons, appears to correlate best with the severity of cognitive deficits and neuropathologic alterations found in this disorder. There is, thus, a need for a marker of choline acetyltransferase activity.

Another imaging agent which has been employed to diagnose Alzheimer's disease with SPECT is $^{123}$I-labeled 3-quinuclidinyl-4-iodobenzilate. This radiopharmaceutical permits in vivo imaging of muscarinic acetylcholine receptor binding function. Alzheimer's disease patients exhibit an impairment of muscarinic receptor binding function relative to a normal age-matched subject. However, $^{123}$I-labeled 3-quinuclidinyl-4-iodobenzilate does not localize, or image, cholinergic neurons.

CAT scanning has been used to determine the size and location of brain tumors, and to determine the degree of brain atrophy that accompanies many neurological disorders. However, CAT scanning techniques are not capable of detecting primary deficits in the cholinergic neurons of the brain. Magnetic resonance imaging (MRI) is likewise deficient in its ability to detect deficits in the cholinergic neurons. There is, therefore, a need for a radiopharmaceutical which enables selective localization and imaging of cholinergic neurons.

Vesamicol, an acetylcholine-storage-blocking drug (available from Research Biochemicals Incorporated, Nattick, MA), is a potent inhibitor of the vesicular sequestration of acetylcholine. Vesamicol, which is chemically denominated trans-2-(4-phenylpiperidino)-cyclohexanol, exhibits enantioselectivity with (−)-vesamicol, which is 25 times more potent than (+)-vesamicol.

VESAMICOL

Structural studies and kinetic data suggest that vesamicol binds to the outside of the storage vesicle membrane at a locus distinct from the active site of the acetylcholine transporter. The blocking activity of many analogs of vesamicol have been reported in Rogers, et al., *J. Med. Chem.*, Vol. 32, No. 6, pp. 1217–1230 (1989). A number of derivatives in the benzovesamicol series are substantially equipotent to vesamicol.

BENZOVESAMICOL

Tritiated Vesamicol has been utilized as a probe for in vitro research on cholinergic neurons. While such radio-tagging does yield radio-emissive compounds, the emission is strictly of the weak β-type, so that any intersecting structure, such as nearby tissue in vivo, may completely absorb, or substantially mask, the emission before the tritium can be detected. Therefore, β-measuring instruments must be very sensitive and intervening tissue absorption must be factored in, thereby increasing the problems created by the use of β-emissive radio-tagged Vesamicol in vivo and limiting its usage to laboratory situations. Thus, a radio-tagged form of Vesamicol having a stronger emissive character would be of substantial benefit to an investigator of the pharmacological actions of Vesamicol.

It is, therefore, an object of this invention to provide a gamma-emitting radiopharmaceutical which localizes selectively in vivo in brain cholinergic neurons.

It is another object of this invention to provide a gamma-emitting radiopharmaceutical for scintigraphic imaging using imaging devices presently found in most nuclear medicine or radiology clinics throughout the country.

It is also an object of this invention to provide a gamma-emitting radiopharmaceutical which can be easily labeled.

It is a further object of this invention to provide a gamma-emitting radiopharmaceutical which can be used to portray density and regional distribution of cholinergic nerves in the brain of patients afflicted with Alzheimer's disease and related neurological disorders.

SUMMARY OF THE INVENTION

The foregoing and other objects are achieved by this invention which provides novel radioactive racemic iodinated benzovesamicol analogs, and its enantiomers, useful as mapping agents for central cholinergic neurons, of the general formula:

where X is selected from the group consisting of H, OH, $NH_2$, NHCO-3-[I]-Ph, and a radioactive isotope of iodine, and Y is selected from the group of H and a radioactive isotope of iodine, Y being H if X contains iodine.

Of course, any radioactive isotope of iodine, such as the clinically used isotopes, $I^{122}$, $I^{123}$, $I^{125}$ and $I^{131}$, can be used in the practice of the invention. $I^{125}$ is preferred for in vitro work in the laboratory due to its relatively long half-life. For radiodiagnostic purposes in humans, $I^{123}$ or $I^{131}$ are isotopes of preference due to their shorter half-lives. The advent of positron emission tomography has also created a use for the positron-emitting $I^{122}$ isotope. The radioiodination procedures may be modified, as known by those of skill in the art, to compensate for the difference in half-life.

Specific illustrative embodiments of the radioactive iodinated benzovesamicol analogs are identified in Table I below:

TABLE I

| X | Y | CHEMICAL FORMULA |
|---|---|---|
| 1) I | H | (±)-trans-2-hydroxy-5-iodo-3-(4-phenylpiperidino)tetralin; |
| 2) H | 6-I | (±)-trans-2-hydroxy-6-iodo-3-(4-phenylpiperidino)tetralin; |
| 3) H | 7-I | (±)-trans-3-hydroxy-6-iodo-2-(4-phenylpiperidino)tetralin; |

TABLE I-continued

| X | Y | CHEMICAL FORMULA |
|---|---|---|
| 4) H | 8-I | (±)-trans-3-hydroxy-5-iodo-2-(4-phenylpiperidino)tetralin; |
| 5) $NH_2$ | 6-I | (±)-trans-5-amino-2-hydroxy-6-iodo-3-(4-phenylpiperidino)tetralin; |
| 6) $NH_2$ | 8-I | (±)-trans-5-amino-2-hydroxy-8-iodo-3-(4-phenylpiperidino)tetralin; |
| 7) OH | 6-I | (±)-trans-2,5-dihydroxy-6-iodo-3-(4-phenylpiperidino)tetralin; |
| 8) OH | 8-I | (±)-trans-2,5-dihydroxy-8-iodo-3-(4-phenylpiperidino)tetralin; |
| 9) NHCO-2-I-Ph | H | (±)-trans-2-hydroxy-5-(2-iodobenzamido)-3-(4-phenylpiperidino)tetralin; |
| 10) NHCO-3-I-Ph | H | (±)-trans-2-hydroxy-5-(3-iodobenzamido)-3-(4-phenylpiperidino)tetralin; and |
| 11) NHCO-4-I-Ph | H | (±)-trans-2-hydroxy-5-(4-iodobenzamido)-(4-phenylpiperidino)tetralin. |

In accordance with a method of use aspect of the invention, a compound having the aforementioned general formula is utilized as a site-specific radioactive tracer compound. An effective detectable amount of the radioactive tracer compound is administered to the body of the living being, preferably intravenously, and permitted to distribute throughout the body of the living being. The distribution pattern of radioactivity produced thereby is externally detected, such as by gamma-camera scintigraphy. In certain embodiments, interface of the gamma-camera to a computer (i.e., computer aided tomography or positron emission tomography) provides an external topological image of the cholinergic nerve endings.

BRIEF DESCRIPTION OF THE DRAWING

Comprehension of the invention is facilitated by reading the following detailed description, in conjunction with the annexed drawing, in which.

DETAILED DESCRIPTION

The invention is a radiolabeled compound, often referred to as a "radiotracer" or a "radiopharmaceutical," of the general formula:

where X is selected from the group consisting of H, OH, $NH_2$, NHCO-3-[I]-Ph, and a radioactive isotope of iodine, and Y is selected from the group of H and a radioactive isotope of iodine, Y being H if X contains iodine. Specific embodiments of the radioiodinated benzovesamicol analogs of the present invention are set forth above in Table I.

The compounds of the present invention selectively localize in the cholinergic neurons of the central nervous system and, therefore, will find applicability in nuclear medicine clinics as radiopharmaceuticals which may advantageously be used in conjunction with conventional imaging equipment to image the human brain. However, it should be noted that, in the peripheral system, the heart and gastrointestinal tract contain a relatively high concentration of cholinergic neurons and, therefore, the inventive radiolabeled compounds may also be useful in imaging these organs.

In particular, the novel radioiodinated benzovesamicol analogs described herein would find applicability for various diagnostic and investigative research purposes, including: (1) to determine the extent and regional location of the neuronal brain damage in Alzheimer's disease patients; (2) to monitor the neuronal-sparing efficacy of future generations of drugs aimed at halting or slowing the ravages of this insidiously progressive disease; (3) to study the etiology of Alzheimer's disease by observing the degree of neuronal involvement in various stages of disease progress; and (4) to screen asymptomatic people at high risk for Alzheimer's disease.

The following examples are directed to methods of making specific embodiments of the invention and are illustrative of the many methods which can be devised by one of ordinary skill in the art for synthesizing the radioiodinated benzovesamicol analogs of the present invention.

In a preferred embodiment, racemic 5-iodobenzovesamicol is synthesized from ($\pm$)-5-aminobenzovesamicol and resolved into the (+)- and (−)-enantiomers. The racemic mixture, or the individual enantiomers, may be radioiodinated to yield the desired radiopharmaceutical compound of the present invention.

EXAMPLE 1

Figure 1:
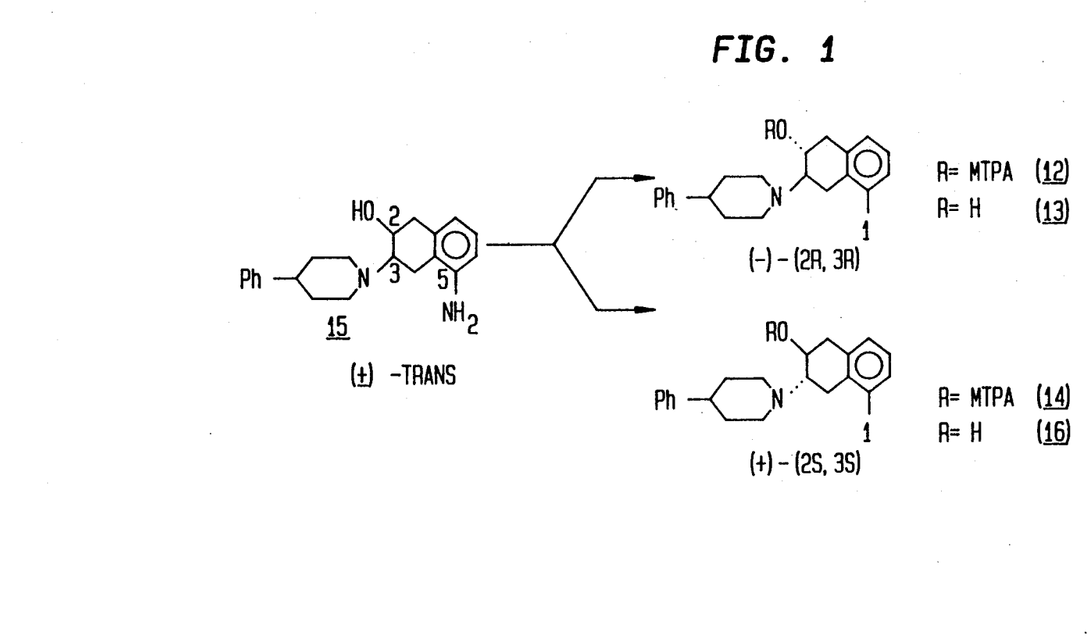
FIG. 1 is a flow chart of an illustrative preparatory scheme for the synthesis of racemic and enantiomeric 5-iodobenzovesamicol from (±)-5-aminobenzovesamicol (compound 15)

FIG. 1 is a flow chart of an illustrative preparatory scheme for the synthesis of ($\pm$)-trans-2-hydroxy-5-iodo-3-(4-phenylpiperidino)tetralin (Compound #1 in Table I; ($\pm$)-5-iodobenzovesamicol) from ($\pm$)-5-aminobenzovesamicol (compound 15 in FIG. 1; ($\pm$)-trans-5-amino-2-hydroxy-3-(4-phenylpiperidino)-tetralin via the diazonium salt through treatment with nitrous acid and reaction with potassium iodide. Compound 15 may be synthesized in accordance with a method discussed hereinbelow in Example 2.

To a cooled (5° C.) solution of ($\pm$)-5-aminobenzovesamicol (120 mg, 0.372 mmol) in acetic acid (2 ml) and concentrated HCl (1 ml), a solution of NaNO₂ (27 mg, 0.395 mmol) in water (2 ml) was added while maintaining the solution temperature under 10° C. The mixture was stirred for 30 minutes and the temperature was maintained below 10° C. Then a solution of KI (74 mg, 0.447 mmol) and I₂ (57 mg, 0.223 mmol) in water (1 ml) was added. The mixture was stirred and maintained under 10° C. for three hours and overnight at room temperature. The reaction mixture was diluted with sat. NaHCO₃ and extracted several times with ether. The ether layers were washed with 10% NaHSO₃, dried over anhydrous Na₂SO₄, and concentrated by evaporation under reduced pressure. The residue was flash-chromatographed on silica with hexane/ethyl acetate (85/15) to afford ($\pm$)-trans-2-hydroxy-5-iodo-3-(4-phenylpiperidino)tetralin as a white solid (109 mg; 68% yield; mp 122° C. when recrystallized from ether/hexane.

Referring to FIG. 1, reaction of ($\pm$)-trans-2-hydroxy-5-iodo-3-(4-phenylpiperidino)tetralin with (−)-(S)-α-methoxy-α-trifluoromethylphenylacetyl (MTPA) chloride results in a mixture of the diasteriormeric MTPA esters, compounds 12 and 14. Separation of esters 12 and 14 was accomplished by thin layer chromatography on silica gel plates eluted with hexane/ethyl acetate (19:1). Base hydrolysis of the MTPA esters provided the pure enantiomers, compounds 13 and 16.

Enantiomeric compound 13 was found to have a negative optical rotation $[\alpha]_D^{23} = -45.4$ (C=1.5, ethanol). By analogy to structural information in the literature, the absolute configuration of compound 13 is (−)-2R,3R. Enantiomeric compound 16 has a positive rotation $[\alpha]_D^{23} = +44.0$ (C=1.5, ethanol). The negative enantiomer was found to be more physiologically active than the positive.

$^{125}$I labeling of the enantiomers was accomplished by solid-phase ion exchange with Na[$^{125}$I]I at 150° C. in the presence of ammonium sulfate as the promoter. The radiochemical purities of [$^{125}$I]-compound 13 and [$^{125}$I]-compound 16 were 97% and 92%, respectively as determined by radio-high performance liquid chromatography (radio-HPLC).

More specifically, enantiomer compound 13 was labeled with $^{125}$I as follows: 20 μg of compound 13, 5 mg of ammonium sulfate, 8.0 mCi of Na[$^{125}$I]I, and 50 μl of deionized water were placed in a 5 ml flask and heated in an oil bath. The reaction flask was equipped with a disposable air-cooled water condenser which in turn was attached to a tandem set of charcoal and aqueous sodium thiosulfate traps to catch any volatile radioiodine. The reaction flask was heated to 150° C. for 25 minutes and then cooled to room temperature. The contents of the reaction flask were dissolved in 2.0 ml methylene chloride and trapped on a silica Sep-Pak cartridge (available from Waters Co., a division of Millipore Corp., Milford, Mass.) and eluted with a gradient of hexane/ethyl acetate to provide radioactive compound 13 with 97% radiochemical purity as determined by radio-HPLC. The optical purity of the radioactive compound 13 was confirmed before and after radioiodine exchange labeling by chiral-radio-HPLC. Specific activity was 170 Ci/mmol as determined by comparison of the ultraviolet spectrum of a known amount of radioactive compound with a UV standard curve.

EXAMPLE 2

Compound 15, chemically known as ($\pm$)-trans-5-amino-2-hydroxy-3-4-phenylpiperidino)tetralin can be synthesized by condensation of an amine with an epoxide derived from a derivative of tetralin.

1-Aminonaphthalene (79 g, 0.55 mol), ethanol (300 ml), t-butyl alcohol (50 ml), and NH₃ (200–300 ml) were placed in a three-necked, round-bottomed flask equipped with a condenser cooled with dry ice. Sodium (30 g, 1.3 mol) was added in portions over a 4 hour period. Then another 50 ml t-butyl alcohol was added. After an hour, 100 ml absolute ethanol was added slowly. This mixture was stirred overnight and then quenched by careful addition of NH₄Cl (50 g) and H₂O (400 ml). The aqueous and organic layers were separated. The aqueous layer was extracted twice with ether. The ether extracts were combined with the organic layer, which was then extracted with H$_2$O (2x) and sat. NaCl. The organic layer was dried over Na$_2$SO$_4$ and filtered through MgSO$_4$. Following evaporation of ether and most of the t-butyl alcohol at 65° C., colorless 1-amino-5,8-dihydronaphthalene was obtained by vacuum distillation (mp 37°–39° C.; yield 97%).

1-Amino-5,8-dihydronaphthalene (60.1 g, 0.414 mol) was dissolved in 200 ml of benzene and cooled to 0° C. Trifluoroacetic anhydride (89 g, 0.42 mol) was added slowly due to the exothermic nature of the reaction. The solution was maintained at 0° C. for an hour. The benzene and trifluoroacetic acid were removed under reduced pressure. More benzene was added and again evaporated in order to aid in removal of the trifluoroacetic acid.

The resultant amide product was dissolved in 300 ml of ether to which was added 3-chloroperoxybenzoic acid (85 g, 80–85% pure). The solution was maintained near 10° C. throughout the addition. Then, the solution was allowed to warm to 23° C. and stirred for 5 hours. The product epoxide, containing some 3-chlorobenzoic acid, was collected by filtration and washed with ether. The solid precipitate was re-suspended in 400 ml of ether, thoroughly washed, and recollected by filtration to yield an epoxide (89.0 g, mp 174°–178.5° C.) Recrystallization of the epoxide from methylene chloride, followed by washing with ether, raised the melting point to 179.5°–181° C.

N-(Trifluoroacetyl)-1-amino-5,8-dihydronaphthalene oxide (1.9 g, 7.4 mmol) was dissolved in 25 ml of absolute ethanol to which was added 4-phenylpiperidine (3.0 g, 19 mmol). The solution was maintained at 45° C. for 17 hours and then refluxed for 3 hours. After cooling to 23° C. for 7 hours, a crystalline solid was collected by filtration and washed with ethanol and carbon tetrachloride. A polar isomer, (±)-trans-8-amino-3-hydroxy-2-(4-phenylpiperidino)tetralin, results from deacylation during the reaction (0.78 g, 33% yield). The mother liquor was evaporated to an oil which was dissolved in carbon tetrachloride. This process was repeated in order to remove most of the ethanol. When the oil was again dissolved in carbon tetrachloride, crystallization commenced and yielded 0.7 g of 4-phenyl-piperidinium trifluoroacetate.

The remaining mother liquor was purified by chromatography on silica gel where N-(trifluoroacetyl)-4-phenylpiperidine was eluted with carbon tetrachloride and a less polar isomer was eluted with carbon tetrachloride/methylene chloride. The yield of the less polar isomer, (±)-trans-5-amino-2-hydroxy-3-(4-phenylpiperidino)tetralin, was 0.84 g, 35% yield. The polar isomer could be crystallized from methylene chloride/ethanol and had a melting point of 217°–218° C. while the less polar isomer had a melting point of 174°–175° C. Their R$_f$ values on silica gel thin layer chromatography in methylene chloride were 0.30 and 0.42, respectively.

EXAMPLE 3

Preparation of
(±)-trans-3-hydroxy-5-iodo-2-(4-phenylpiperidino)tetralin (Compound #4 on Table I)

A solution of NaNO$_2$ (185 mg, 2.68 mmol) in water (2 ml) was added to a cooled (5° C.) solution of (±)-8-aminobenzovesamicol (816 mg, 2.53 mmol; prepared in a manner similar to that described in Example 1) in acetic acid (15 ml) and concentrated HCl (2 ml); while the solution temperature was maintained under 10° C. The resulting mixture was stirred for 30 minutes and maintained at a temperature below 10° C. Then a solution of KI (504 mg, 3.4 mmol) and I$_2$ (385 mg, 1.52 mmol) in H$_2$O (1 ml) was added. This mixture was stirred and maintained at a temperature less than 10° C. for 3 hours and at room temperature overnight. The reaction mixture was diluted with sat. NaHCO$_3$ and extracted several times with ether. The ether layers were washed with 10% NaHSO$_3$, dried over anhydrous Na$_2$SO$_4$, and concentrated by evaporation under reduced pressure. The residue was flash-chromatographed on silica with hexane/ethyl acetate (85/15) to afford (±)-trans-3-hydroxy-5-iodo-2-(4-phenylpiperidino)tetralin as a white solid (623 mg; 57% yield; mp 194° C. when recrystallized from ether/hexane).

EXAMPLE 4

Preparation of
(±)-trans-5-amino-2-hydroxy-8-iodo-3-(4-phenylpiperidino)tetralin (Compound #6 on Table I)

A solution of ICl (78.5 mg, 0.484 mmol) in acetic acid (5 ml) was added drop-wise to a solution of (±)-5-aminobenzovesamicol (156 mg, 0.484 mmol) in acetic acid (5 ml). The mixture was stirred for 30 minutes at room temperature and concentrated by evaporation under reduced pressure. The residue was diluted with sat. NaHCO$_3$ and extracted several times with ethyl acetate. The extracts were washed with brine, dried over anhydrous Na$_2$SO$_4$, and concentrated by evaporation under reduced pressure. The residue was flash-chromatographed on silica with hexane/ethyl acetate (60/40) to afford (±)-trans-5-amino-2-hydroxy-8-iodo-3-(4-phenylpiperidino)tetralin as a white solid (188 mg; 87% yield; mp 195° C. when recrystallized from ethyl acetate/hexane).

EXAMPLE 5

Preparation of
(±)-trans-2-hydroxy-5-(3-iodobenzamido)-3-(4-phenylpiperidino)tetralin (Compound #10 on Table I)

To a solution of 1-amino-1,8-dihydronapthalene (1.76 g, 12.9 mmol) in triethylamine (2 ml) and benzene (10 ml) was added a solution of 3-iodobenzoyl chloride (3.22 g, 12.09 mmol) in benzene (5 ml). The resulting solution was stirred for 4 hours at room temperature and poured into a solution of sat. NaHCO$_3$. The aqueous layer was extracted with ether. The extract was dried over MgSO$_4$ and concentrated by evaporation under reduced pressure to yield 4.12 g of the amide (91% yield).

A solution of m-chloroperoxybenzoic acid (2.05 g, 10.11 mmol) in CHCl$_3$ (200 ml) was added drop-wise to a cooled (10° C.) solution of the amide (3.45 g, 9.20 mmol) in CHCl$_3$. The mixture was allowed to warm to room temperature, stirred for 6 hours, and poured into sat. NaHCO$_3$. The aqueous layer was extracted with CH$_2$Cl$_2$. The extract was dried over MgSO$_4$ and concentrated by evaporation under reduced pressure to yield 2.70 g of the epoxide (75% yield).

A solution of the epoxide (1.17 g, 2.99 mmol) and 4-phenylpiperidine (508 mg, 3.15 mmol) in ethanol (10 ml) was refluxed for two days. The mixture was concentrated by evaporation under reduced pressure and the residue was flash-chromatographed on silica with hexane/ethyl acetate (60/40) to separate two isomers. The yield of 5-(3-iodobenzamido)benzovesamicol as a less polar compound was 692 mg (42%) and the yield of 8-(3-iodobenzamido)benzovesamicol as a more polar compound was 681 mg (41%). The melting point of 5-(3-iodobenzamido)benzovesamicol, or (±)-trans-2-hydroxy-5-(3-iodobenzamido)-3-(4-phenylpiperidino)-tetralin, was 110° C.

Radioiodination of the Iodinated Benzovesamicol Analogs

Radioiodination of the iodinated benzovesamicol analogs disclosed herein, or one of the intermediates in the synthesis pathway, can be accomplished by a variety of techniques, some of which are known in the art. For example, aromatic compounds with electron donating groups (such as anilines) can be radiolabelled by electrophilic iodination in the presence of radioiodine, iodine monochloride, chloramine-T, iodogen, etc. Unactivated aromatic rings, can be radioiodinated by exchange of a leaving group, such as aryl boronic acids, aryl thallium trifluoroacetates, triazenes or metallated arenes with radioiodine. Direct electrophilic radioiodination of a phenyl ring is yet another alternative, but may result in the production of isomeric mixtures which are difficult to separate. Iodine exchange of aryl iodides with radioiodine may be a preferably approach insofar as no complex separation techniques are necessary since the substrate and radioiodinated product are chemically identical. In yet another exemplary embodiment, an isotope exchange-type technique may be utilized wherein the substrate and radioiodine are reacted at an elevated temperature in a "melt." The molten reaction medium possesses a sufficiently high dielectric constant to solubilize both the substrate and radioiodine. Examples of reaction media currently in use are benzoic acid (mp 122° C., bp 249° C.) and acetamide (mp 82° C., bp 221° C.).

In an advantageous preferred embodiment of the invention, no-carrier added [$^{125}$I]-(±)-5-iodobenzovesamicol (or (±)-trans-2-hydroxy-5-[$^{125}$I]-iodo-3-(4-phenylpiperidino)tetralin) was synthesized by radioiodinating a tin compound. Example 6 describes a method of preparing the tin compound, (±)-trans-5-(tri-n-butyltin)-2-hydroxy-3-(4-phenylpiperidino)tetralin.

EXAMPLE 6

A solution of 5-Iodobenzovesamicol (0.10 g, 0.23 mmol) in 2 ml of dry toluene was degassed by bubbling argon through the solution for 5 minutes. The solution was then treated with bis(tributyltin) (0.298 g, 0.51 mmol) and tetrakis(triphenylphosphine) palladium (0), (0.015 g, 0.013 mmol), and refluxed under argon for 18 hours. The toluene was removed by rotoevaporation and the residue was flash-chromatographed on silica with hexane/ethyl acetate (85/15) to yield a white crystalline product, (±)-trans-5-(tri-n-butyltin)-2-hydroxy-3-(4-phenylpiperidino)tetraline.

Aqueous hydrogen peroxide (50 μl, 3% w/v) was added to a mixture of 50 μl of the tin derivative prepared in Example 6 (1 mg/ml of ethanol), 50 μl of 0.1N HCl, and 5 μl of Na[$^{125}$I]I (3-4 mCi, carrier-free; specific activity 2200 Ci/mmol) in a polypropylene tube. The reaction was run at 23° C. for 15 minutes and then terminated by the addition of 0.1 ml of sodium bisulfite (300 mg/ml). The reaction solution was neutralized by the addition of saturated sodium bicarbonate solution and then extracted with 1 ml ethyl acetate (3x). The combined organic layers were dried over anhydrous sodium sulfate and then analyzed by radio-TLC using silica and chloroform/ethanol/ammonium hydroxide (97/3/0.1); $R_f$ of [$^{125}$I]-(±)-IBVM is 0.65; $R_f$ of sodium [$^{125}$I] iodide is 0.0. The ethyl acetate was concentrated to dryness by rotoevaporation and the residue was purified further by reverse-phase HPLC. The radiochemical yield was 99% with a radiochemical purity of 99%. Chiral-HPLC was used to separate the racemic mixture.

EXAMPLE 7

Figure 2:
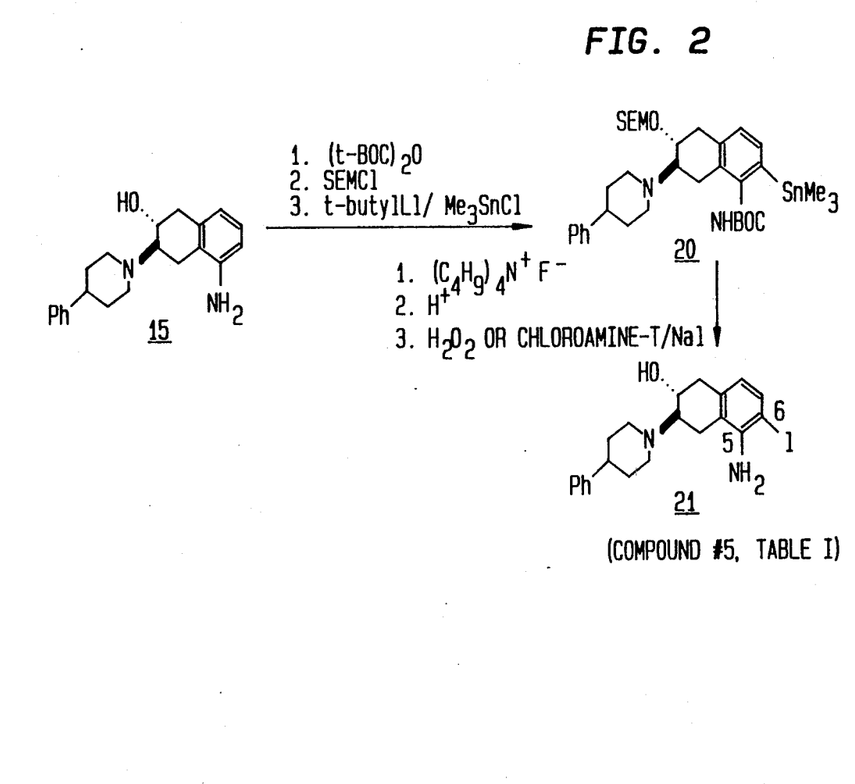
FIG. 2 is an illustrative preparatory scheme for synthesis of (±)-trans-5-amino-2-hydroxy-6-iodo-3-(4-phenylpiperidino)tetralin (compound 5 on Table I)

FIG. 2 is an illustrative preparatory scheme for synthesis of (±)-trans-5-amino-2-hydroxy-6-[$^{125}$I]-iodo-3-(4-phenylpiperidino)tetralin (Compound 5 on Table I). (±)-trans-5-Amino-2-hydroxy-3-(4-phenylpiperidino)-tetralin is reacted with ditert-butyl dicarbonate (available from Waters Co., a division of Millipore Corp., Milford, Mass.); 2-(trimethysilyl)-ethoxymethyl chloride; t-butyl lithium and trimethyl tin chloride to form compound 20. Compound 20 is reacted with tetrabutyl ammonium fluoride and hydrolyzed. An isotope exchange reaction with Na[$^{125}$I]I in the presence of peroxide or chloramine-T results in the production of carrier-free (±)-trans-5-amino-2-hydroxy-6-iodo-3-(4-phenylpiperidino)tetralin, compound 21.

EXAMPLE 8

Radioiodination of (±)-trans-5-amino-2-hydroxy-8-iodo-3-(4-phenylpiperidino)tetralin (Compound 6 on Table I)

In sequential order, the following compounds were added to a polypropylene tube (Sarstedt, FRG): (±)-5-aminobenzovesamicol (100 μg in 50 μl of 13.5 mM HCl), 0.3M potassium phosphate buffer (50 μl, pH 6.75), and aqueous Na$^{125}$I (4.0 mCi in 5 μl of 0.1N NaOH). The reaction was initiated by the addition of aqueous chloramine-T (20 μl, 0.34 mg/ml). After standing for 5 minutes at room temperature, the reaction was quenched with aqueous sodium dithionite (300 μl, 1 mg/ml) followed by aqueous 1N NaOH (180 μl). The aqueous solution was extracted (3x) with ethyl acetate (1 ml). The solution was vortexed during each extraction to facilitate mixing and separation of the organic and aqueous layers. The organic ethyl acetate layer was removed with a Pasteur pipette. The ethyl acetate layer, which contained 4.85 mCi of product, was analyzed by radio-TLC on silica gel with chloroform/methanol/ammonium hydroxide (95/5/0.1). (±)-trans-5-Amino-2-hydroxy-8-[$^{125}$I]iodo-3-(4-phenylpiperidino)tetralin was produced with 99% radiochemical purity by radio-TLC ($R_f$ of product=0.52; $R_f$ of starting material =0.50) and 97% radiochemical yield.

The above-described radioiodinated analogues may be solubilized in a suitable transport agent, or carrier vehicle, and administered to mammalian subjects as radiologic agents by any known manner, preferably intraparentrally such as intravenously or intraperitoneally. Of course, the novel compounds of the present invention can be provided as salts thereof, having a form such as hydrochloride, tartrate, citrate, bromide, chloride, or sulfate.

In Vivo Studies:

EXAMPLE 9

Female CD-1 mice (available from Charles River, Wilmington, Mass; 18-27 g) (n=4-5/tracer) were injected under ether anesthesia via the tail vein with 7.2-10.8 μCi of racemic [$^{125}$I]-iodobenzovesamicol (IBVM) or its optical isomers, compounds 13 and 16, (prepared by the method of Example 1; specific activity ranged from 105-170 Ci/mmol) or 5.0 μCi of [$^3$H]-(−)-vesamicol (New England Nuclear; specific activity=57 Ci/mmol). The mice were sacrificed 4 hours post-injection and the tissues were excised, weighed, and counted in an autogamma counter or a liquid scintillation counter. The tissue concentrations were normalized to a 25 g mouse. The results are shown below in Table II.

hour cortical or striatal activity of the (+)-enantiomer as an estimate of non-neuronal binding of the (−)-enantiomer in these two brain areas, the same value calculated above (>95%) is obtained for the 4-24 hour neuronal specificity of compound 13. Further support for the high neuronal specificity of compound 13 can be obtained by comparison of the regional distribution pattern of the enantiomers in heart tissue. The concentrations of acetylcholine and ChAT in mammalian heart indicate a density of ventricular cholinergic innervation

TABLE II

RADIOTRACER CONCENTRATION IN MOUSE 4 h AFTER INTRAVENOUS INJECTION

| TRACER | CONCENTRATION (% DOSE/G ± S.D.) | | | % OF DOSE INJECTED |
|---|---|---|---|---|
| | CEREBRAL CORTEX | STRIATUM | CEREBELLUM | WHOLE BRAIN |
| [$^{125}$I]-(−)-IBVM | 2.56 ± .21 | 6.26 ± .46 | 0.23 ± .04 | 1.03 ± .07 |
| [$^{125}$I]-(±)-IBVM | 1.17 ± .20 | 3.29 ± .52 | 0.20 ± .04 | 0.56 ± .07 |
| [$^{125}$I]-(+)-IBVM | 0.12 ± .01 | 0.26 ± .04 | 0.06 ± .01 | 0.06 ± .01 |
| [$^3$H]-(−)-Vesamicol | 0.42 ± .03 | 0.40 ± .11 | 0.10 ± .02 | 0.24 ± .02 |

| TRACER | CONCENTRATION RATIOS | | | |
|---|---|---|---|---|
| | [STRIATUM] [CEREBELLUM] | [CORTEX] [CEREBELLUM] | [CORTEX] [BLOOD] | [L. ATRIUM] [L. VENTRICLE] |
| [$^{125}$I]-(−)-IBVM | 27.2 | 11.1 | 6.2 | 5.5 |
| [$^{125}$I]-(±)-IBVM | 16.5 | 5.9 | 2.3 | 4.7 |
| [$^{125}$I]-(+)-IBVM | 4.3 | 2.0 | 0.3 | 0.9 |
| [$^3$H]-(−)-Vesamicol | 4.0 | 4.2 | 0.8 | 0.1 |

Table II compares the accumulation of radioactivity in three regions of mouse brain following intravenous administration of the specified tracer compounds: [$^{125}$I]-iodobenzovesamicol or its optical isomers, compounds 13 and 16, and [$^3$H]-(−)-vesamicol. The marked accumulation of radioactivity in the striatum and cerebral cortex following intravenous injection of the (−)-enantiomer, compound 13, is consistent with the high density of cholinergic innervation in these two brain regions. Choline acetyltransferase (ChAT) activity, the best marker for cholinergic nerves, is present in striatum, cerebral cortex, and cerebellum of the adult rat in approximate ratios of 26 to 9 to 1, respectively. The low striatal and cortical accumulation of the (±)-enantiomer, compound 16, is consistent with the stereospecificity of vesamicol blockage of acetylcholine storage observed in vitro.

Figure 3:
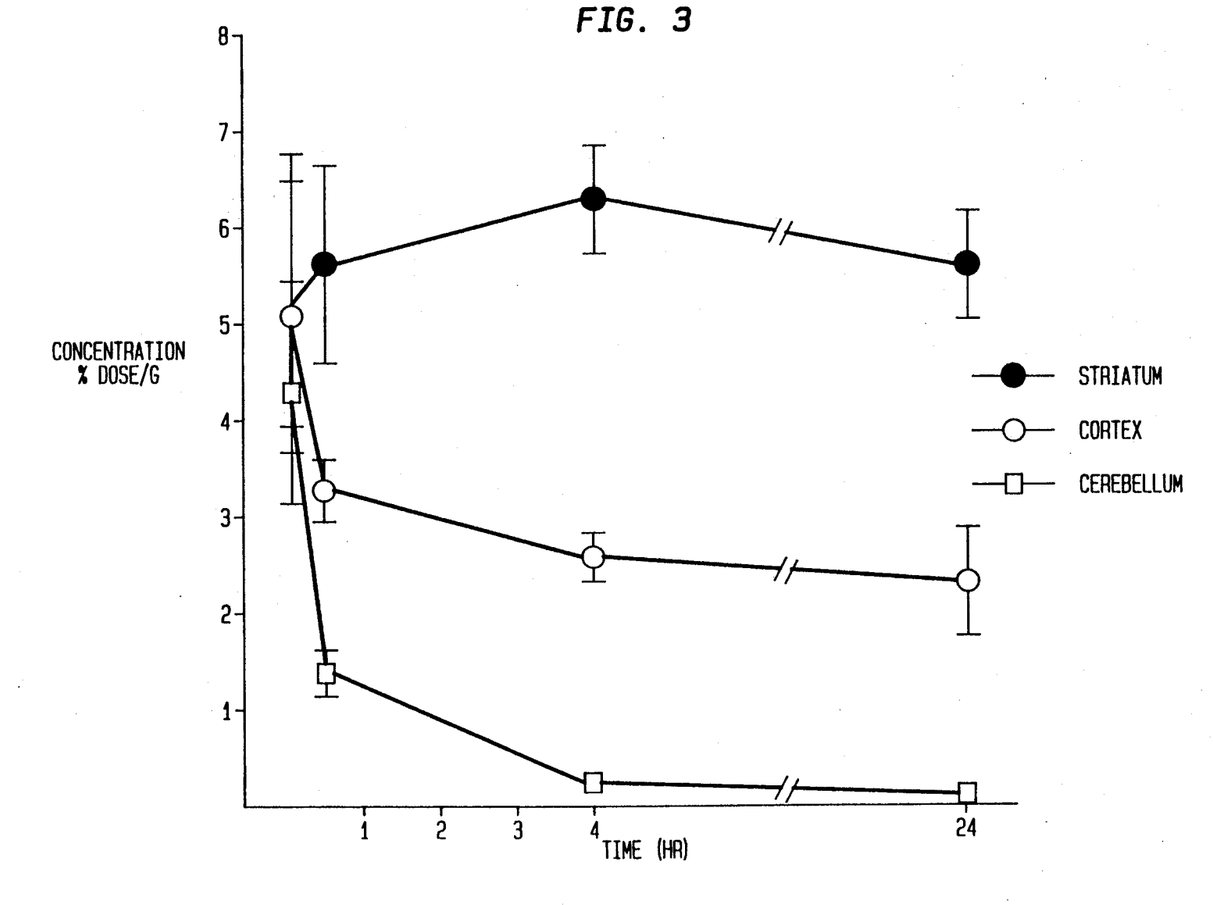
FIG. 3 is a temporal pattern of distribution of [$^{125}$I]-(−)-5-iodobenzovesamicol in the brain of female CD-1 mice (N=4-5 per time point). Tissue concentrations are normalized to a 25 g mouse.
Figure 4:
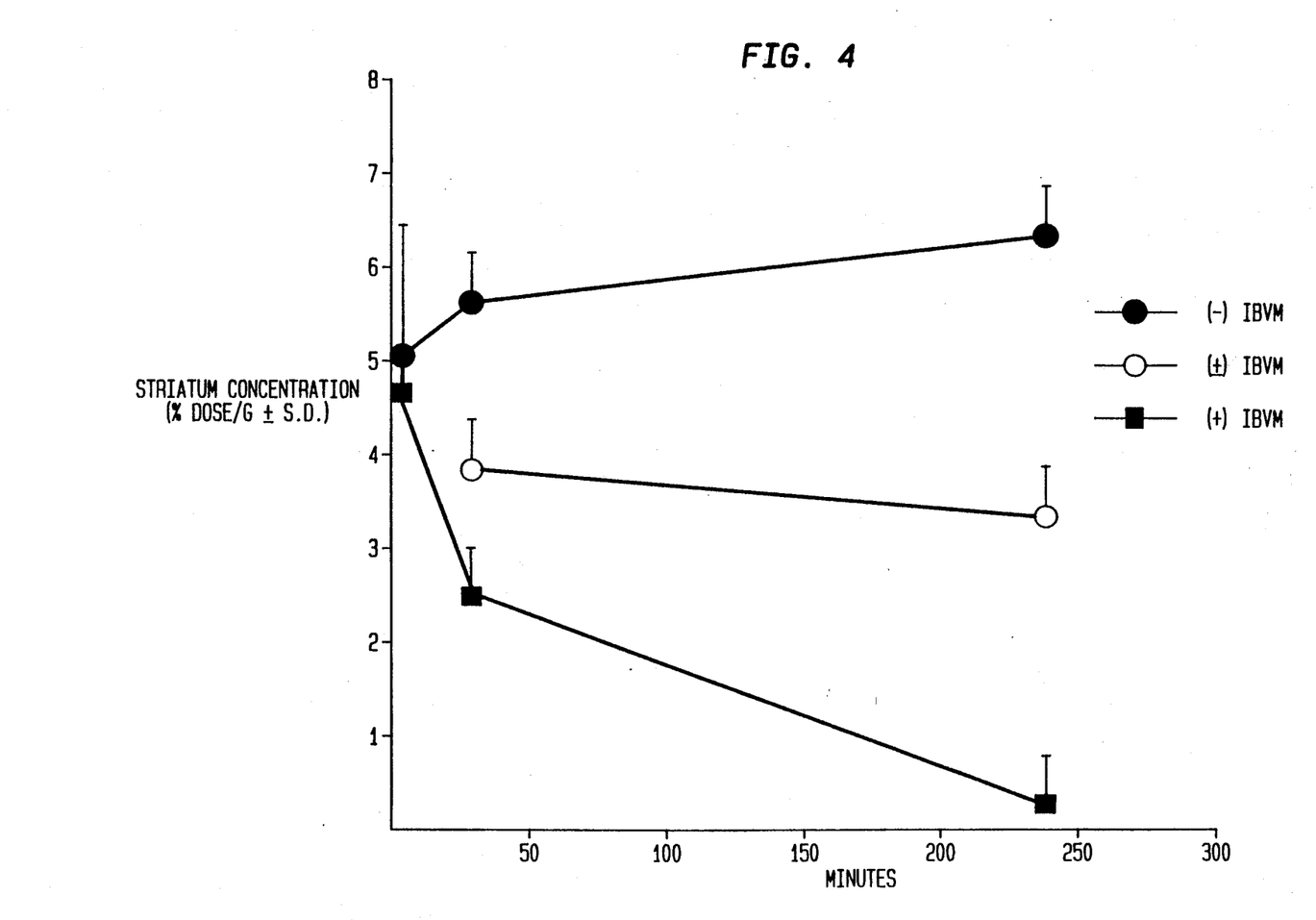
FIG. 4 is a comparison of the striatum concentrations of [$^{125}$I] labeled enantiomers of 5-iodobenzovesamicol in female CD-1 mice (N=4-5 animals per time point). Tissue concentrations are normalized to a 25 g mouse.

Tissue distribution results are shown in FIGS. 3 and 4. FIG. 3 shows that from 4 to 24 hours following injection of compound 13, the radioactivity in the cerebral cortex and striatum remains at a high and fairly constant level. Using the cerebellar concentration during this time period as an approximation of non-neuronal binding, it can be seen from FIG. 3 that the specific neuronal binding of compound 13 in cortex and striatum from 4 to 24 hours is >95%.

FIG. 4 compares the time-activity curves of the two labeled enantiomers, compounds 13 [(−)-IBVM] and 16 [(+)-IBVM], in mouse striatum. The two tracers show nearly identical initial striatal uptake, but the (+)-isomer rapidly washes out of the striatum, and within 4 hours is nearly absent from this tissue. If one uses the 4 that is about 1/5 that of the atria. At 4 hours, the left atrium-to-left ventricle concentration ratio of the (−)-isomer compound 13 is 5.5 compared to a ratio of 0.9 for the (+)-isomer compound 16.

Pretreatment of mice with unlabeled (−)-vesamicol hydrochloride (605 μg/kg, i.p.), 10 minutes prior to tracer injection lowers the 4 hour striatal and cortical accumulation of [$^{125}$I]-Compound 13 by 65%. However, this decrease is most likely an underestimation of the extent of neuronal binding of [$^{125}$I]-Compound 13 since larger doses of (−)-vesamicol could not be injected due to toxicity limitations. Also, as shown in the results of Table II, the retention of [$^3$H]-(−)-vesamicol in brain at 4 hours is comparatively low, suggesting that putative blocking doses of vesamicol would likely clear more rapidly from the brain than tracer levels of 5-iodobenzovesamicol.

EXAMPLE 10

Radioactive compound 13 as prepared above in Example 1 was dissolved in ethanol/0.005M sodium acetate (1/9) buffer (pH 4.5) at 1 mCi/ml and 10 μCi of the solution was administered intravenously to lightly etherized CD-1 mice. Animals were sacrificed at various time points after injection. Samples of the brain and other tissues were excised, weighed, and counted. As shown below in Table III, the ratios at 4 hours are consistent with the regional distribution pattern of central cholinergic neurons. Pretreatment of mice with cold (±)-vesamicol (0.53 mg/kg, ip) diminished striatal and cortical accumulation of radioactivity (−53%) and cerebellum accumulation (−8%).

TABLE III

BRAIN DISTRIBUTION OF 5-[$^{125}$I] IODOBENZOVESAMICOL IN MICE[a]

| GROUP | CONCENTRATION (% Dose/g) | | | | TISSUE RATIOS | |
|---|---|---|---|---|---|---|
| | STRIATUM | CORTEX | CEREBELLUM | BLOOD | STRIATUM CEREBELLUM | CORTEX CEREBELLUM |
| Control | 4.12 ± .65 | 1.46 ± .25 | 0.26 ± .06 | 1.01 ± .70 | 15.8 | 5.6 |

TABLE III-continued
BRAIN DISTRIBUTION OF 5-[$^{125}$I] IODOBENZOVESAMICOL IN MICE[a]

| | CONCENTRATION (% Dose/g) | | | | TISSUE RATIOS | |
| | | | | | STRIATUM | CORTEX |
| GROUP | STRIATUM | CORTEX | CEREBELLUM | BLOOD | CEREBELLUM | CEREBELLUM |
| --- | --- | --- | --- | --- | --- | --- |
| Blocked[b] | 1.97 ± .35 | 0.69 ± .13 | 0.24 ± .10 | 0.450 ± .100 | 8.2 | 2.9 |

[a]N = 5 per group. Mice (CD-1) weighed 19-21 g. Concentrations are normalized to a 20 g mouse.
[b]Blocking dose (0.53 mg/kg, ip) of (±)-vesamicol was given 10 min prior to i.v. tracer injection; all amimals were killed 4 h after tracer injection. Controls received an equal volume of vehicle. In vivo autoradiography in rat 90 min after i.v. injection of 5-[$^{125}$I]IBVM confirms the selective accumulation of tracer in the striatum.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are profferred to facilitate comprehension of the invention, and should not be construed to limit the scope thereof.

What is claimed is:

1. A compound selected from the group consisting of benzovesamicol analogs of the general formula:

where X is selected from the group consisting of H, OH, NH$_2$, NHCO-3-[I]-Ph, and a radioactive isotope of iodine, and Y is selected from the group of H and a radioactive isotope of iodine, Y being H if X contains iodine, wherein, at least one of X or Y contains a radioactive isotope of iodine.

2. The compound of claim 1 wherein said radioactive isotope of iodine is selected from the group consisting of $^{122}$I, $^{123}$I, $^{125}$I, and $^{131}$I.

3. The compound of claim 1 which is (±)-trans-2-hydroxy-5-iodo*-3-(4-phenylpiperidino)tetralin.

4. The compound of claim 1 which is (±)-trans-2-hydroxy-6-iodo*-3-(4-phenylpiperidino)tetralin.

5. The compound of claim 1 which is (±)-trans-3-hydroxy-6-iodo*-2[-2]-(4-phenylpiperidino)tetralin.

6. The compound of claim 1 which is (±)-trans-3-hydroxy-5-iodo*-2-(4-phenylpiperidino)tetralin.

7. The compound of claim 1 which is (±)-trans-5-amino-2-hydroxy-6-iodo*-3-(4-phenylpiperidino)tetralin.

8. The compound of claim 1 which is (±)-trans-5-amino-2-hydroxy-8-iodo*-3-(4-phenylpiperidino)tetralin.

9. The compound of claim 1 which is (±)-trans-2,5-dihydroxy-6-iodo*-3-(4-phenylpiperidino)tetralin.

10. The compound of claim 1 which is (±)-trans-2,5-dihydroxy-8-iodo*-3-(4-phenylpiperidino)tetralin.

11. The compound of claim 1 which is (±)-trans-2-hydroxy-5-(2-iodo*benzamido)-3-(4-phenylpiperidino)-tetralin.

12. The compound of claim 1 which is (±)-trans-2-hydroxy-5-(3-iodo*benzamido)-3-(4-phenylpiperidino)-tetralin.

13. The compound of claim 1 which is (±)-trans-2-hydroxy-5-(4-iodo*benzamido)-3-(4-phenylpiperidino)-tetralin.

14. A method of scintigraphy imaging of the brain which comprises administering to the body of a mammalian test subject an effective radioactivity producing amount of a radiologic agent comprising the compound as set forth in claim 1 and detecting the radioactivity.

15. A method of computed tomography visualization of the brain which comprises administering to the body of a mammalian test subject an effective contrast-producing amount of a radiologic agent comprising the compound as set forth in claim 1 and detecting.

* * * * *